United States Patent [19]

van de Werken

[11] Patent Number: Plant 7,575

[45] Date of Patent: Jul. 2, 1991

[54] FORSYTHIA CV. 'TINKLE BELLS'

[75] Inventor: Hendrik van de Werken, Knoxville, Tenn.

[73] Assignee: The University of Tennessee Research Corporation, Knoxville, Tenn.

[21] Appl. No.: 273,489

[22] Filed: Nov. 21, 1988

[51] Int. Cl.[5] ..... A01H 5/00

[52] U.S. Cl. ..... Plt./54

[58] Field of Search ..... Plt./54

[56] References Cited

PUBLICATIONS van de Werken (1988) "Mutant Offspring", *American Nurseryman,* vol. 167, No. 1 (Jan. 1, 1988) pp. 127-132.

Fincham, J. R. S., "Ionizing Radiation", *Genetics,* Jones and Bartlett Publishers, Inc., Boston, 1983, pp. 326-333.

Decourtye, L., (1978) "Utilisation de la Mutagenèse pour l'Obtention de Nouvelles Variétés d'Arbustes Ornementaux", (DIALOG English Abstract) Comptes Rendus des Seances de l'Academie d'Agriculture de France, vol. 64 (8), pp. 664-669.

"Arnoldia," vol. 31, No. 2, The Arnold Arboretum, Mar. 1971, pp. 41-63.

"Flowering Shrubs," Zucker, Isabel, 1966, D. Van Nostrand Co., Inc., New York, N.Y., p. 380.

"Hilliers Manual of Trees & Shrubs," 2nd American Edition, Hilliers & Sons Ltd., 1979, A. S. Barnes & Co., Cranbury, N.J., p. 575.

"Hortus Third, A Concise Dictionary of Plants Cultivated in the United States and Canada," Staff of L. H. Bailey Hortorium, Cornell University, 1976, MacMillan Publishing Co., New York, N.Y., p. 1290.

"Manual of Woody Landscape Plants—Their Identification, Ornamental Characteristics, Propagation and Uses," Dirr, Michael A., 1983, Stipes Publishing Co., Champaign, Ill., p. 826.

*Primary Examiner*—James R. Feyrer

*Attorney, Agent, or Firm*—William H. Elliott, Jr.

[57] ABSTRACT

A new cultivar of *Forsythia intermedia* named 'Tinkle Bells' characterized by its floriferousness, its semi-dwarf, upright character, its downwardly directed flowers, and its leaves which are serrated only at their upper ends.

3 Drawing Sheets

This invention relates to a new cultivar of *Forsythia intermedia* named "Tinkle Bells", which is characterized especially by its semi-dwarf character, its upright growth habit, its pendulous flower buds and flowers, and the acute leaf tips on flowering wood foliage.

The new variety is a vegetative selection derived from a vegetative line of mutants, which had been produced in turn by subjected rooted cuttings of the parent *Forsythia intermedia* "Lynwood Gold" (*F. intermedia* "Spectabilis") to irradiation with 1,200 rad fast neutrons.

In 1968, three hundred cuttings of "Lynwood Gold" that had been potted and held in cold storage (38° F.) for six weeks and then returned to the greenhouse for two days were irradiated with 1200 rad fast neutrons. One of the plants of this group that broke dormancy formed a shoot with variegated foliage. This plant was cut back repeatedly to induce branching and eventually formed shoots that exhibited different characteristics. Each shoot was propagated by stem cuttings over 10 vegetative generations of selection and propagation. From this plant population two vegetatively selected types and three seedlings were selected. Further propagation and testing of these selections over several more years were shown to be the stable and new forsythia varieties that are the subject of this and four other copending plant patent applications; viz:

| Ser. No. | Name | Type |
|---|---|---|
| 272,063 | "Lemon-Screen" | vegetative selection |
| 273,489 | "Tinkle Bells" | vegetative selection |
| 271,919 | "Minikin" | seedling |
| 271,665 | "Fairy Land" | seedling |

-continued

| Ser. No. | Name | Type |
|---|---|---|
| 271,666 | "Pygmy-Red" | seedling |

Each differs greatly from the parent "Lynwood Gold" and also from one another.

"Tinkle Bells" was selected from a group of vegetatively propagated shoots because it was very floriferous and attractive when in bloom. Cuttings from this plant have been rooted in soil and asexually propagated, and its progeny have displayed homogenous and stable characteristics.

Throughout this specification, color names beginning with a small letter signify that the name of the color as used in common speech are aptly descriptive. Color names beginning with a capital letter designate values based on the R.H.S. Colour Chart, published by The Royal Horticultural Society of London, England.

The accompanying drawings illustrate the new variety in color as grown in Knox County within the State of Tennessee.

Figure 1:
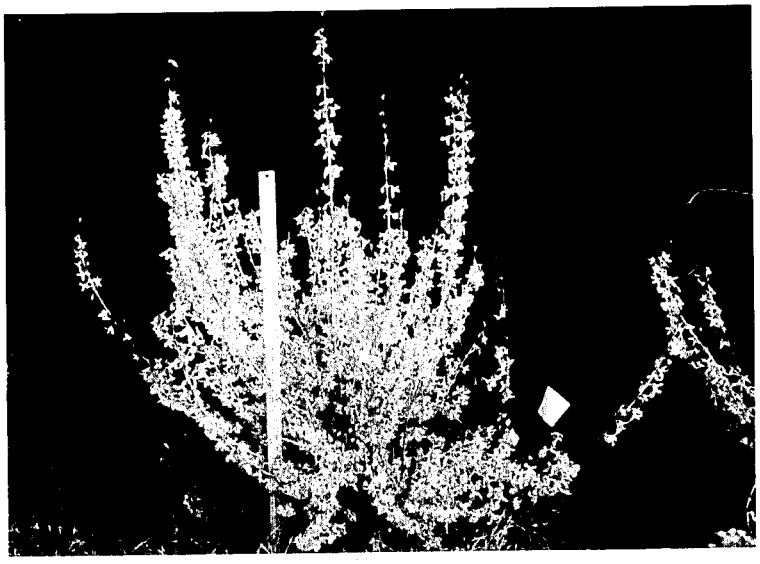
FIG. 1 illustrates a five year old "Tinkle Bells" plant in spring bloom.
Figure 2:
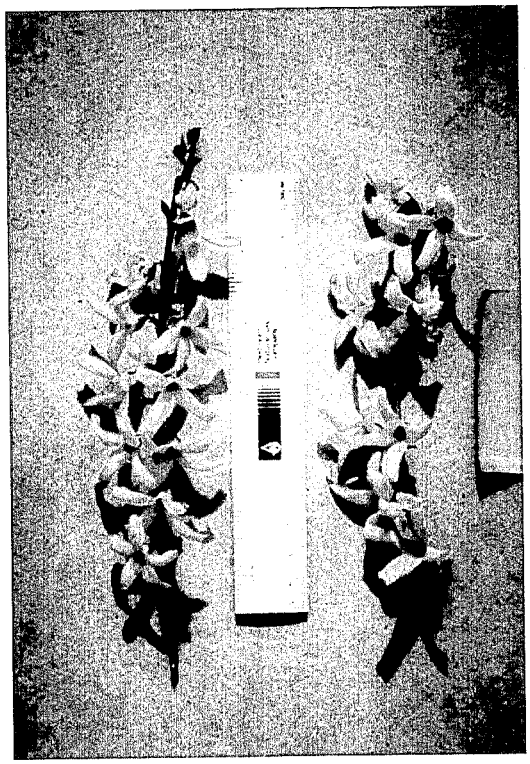
FIG. 2 shows flowered cut stems.
Figure 3:
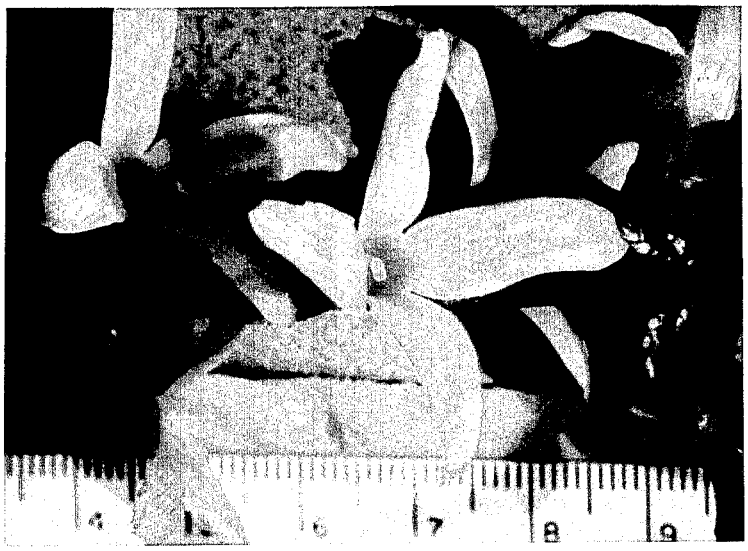
FIG. 3 is a close-up view of the flowers of FIG. 2.
Figure 4:
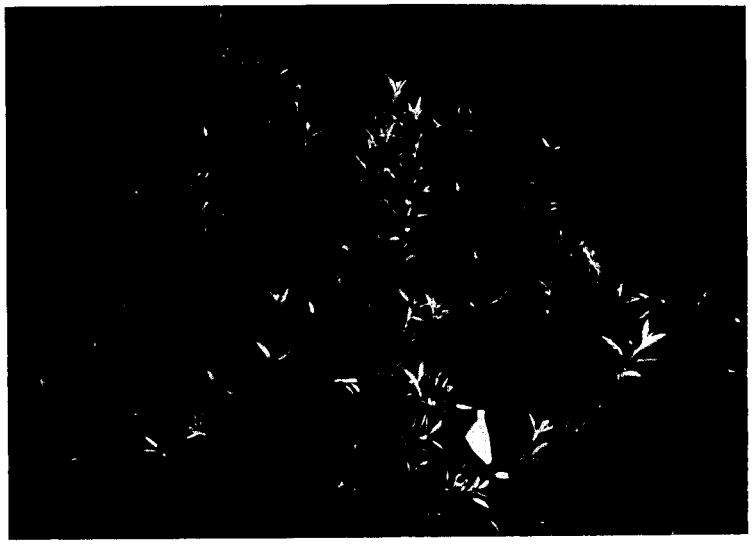
FIG. 4 illustrates the "Tinkle Bells" plant in summer foliage.
Figure 5:
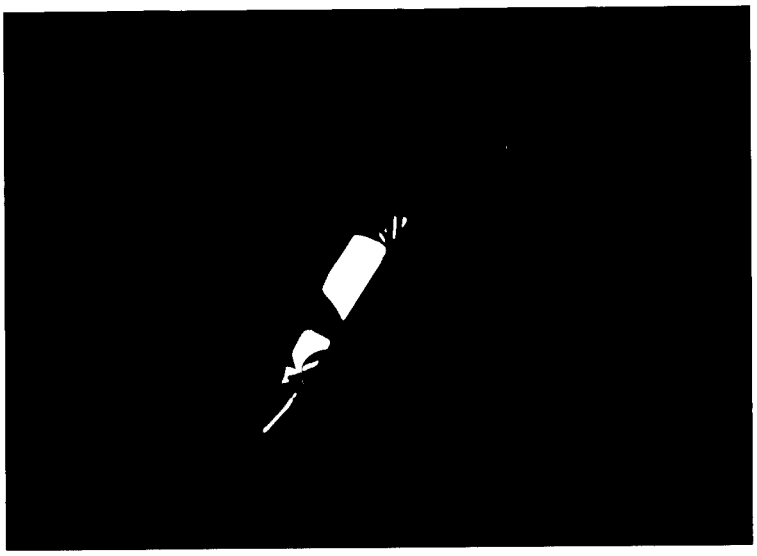
FIG. 5 is a closer view of the foliage shown in FIG. 4.

The following characteristics distinguish "Tinkle Bells" from its parent and other Forsythia cultivars:

THE PLANT

Although "Tinkle Bells", like its parent "Lynwood Gold", exhibits an upright growth habit, the ultimate height of "Tinkle Bells" is 4 to 4½ ft. The plant exhibits medium vigor and is hardy in Zone 6b or lower. Because of its upright habit, "Tinkle Bells" tends not to self propagate by natural layerage, but the plant expands by stooling, i.e., shoots arise from the ground around the base of the plant, and the stooling can be controlled with post-emergence herbicides. Its upright growth habit and flowering at an early age make "Tinkle Bells" suitable for container growth and forcing. "Tinkle Bells" has a number of landscape applications, particularly for border and low screen plantings. The plant requires minimal pruning and has disease and insect-resistant foliage.

Its parent, "Lynwood Gold", by contrast is tall and slender—a straight upright variety with erect stems and which attains a height of 6 ft. to 7½ ft. at maturity.

SHOOTS

The stems of "Tinkle Bells" are yellow green when young and light brown when mature. The stems are rigid and the pith is sparsely lamellate between nodes.

The stems of the "Lynwood Gold" parent are green when young and brown when mature; they are a bit stiff; the pith at the nodes is lamellate, and on one year shoots, the stems between nodes are hollow.

FLOWER

"Tinkle Bells" flower early with bright yellow flowers (Yellow 7B) which generally have four, but occasionally five or six petals; the corolla is ½ inch long, opening up to approximately a 45 degree angle with a total spread of ½ in. to ¾ in. The pollen sacs of the stamen are located slightly below the stigmas of the short pistils. The plant generally produces two, but often four flowers per node on the flowering wood, which has internodes ½ to 1½ in. long. Both the buds and resultant flowers are pendulous on upright stems.

The "Lynwood Gold" parent is fertile and has pistils that extend well above its pollen sacs, is late flowering and its medium sized flowers (about 1" to 1½" in diameter) are almost evenly spaced on the stem. The flowers of "Lynwood Gold" are brilliant yellow (lighter than its parent, *F. spectabilis*). The corolla lobes of "Lynwood Gold" are reflexed and its petals are large, broad open and elliptic.

FOLIAGE

The "Tinkle Bells" leaves are medium green both in the young and mature stage. The leaves are simple elliptical, generally serrate, but only on the upper one-third, near the tip. The leaves are acute on flowering shoots and acuminate on vegetative shoots. The leaves are ½ in. wide and, including the petiole, are 2 in. to 3 in. long.

The leaves of the "Lynwood Gold" parent, on the other hand, are ovate lanceolate in shape and about 3" to 4½" long and about 1" to 1½" wide. Both young and old leaves are deep green in color.

To facilitate the comparison of the characteristics and features of "Tinkle Bells", the subject of this application, and its parent, "Lynwood Gold" and also with the four other new mutant offspring varieties of "Lynwood Gold" referred to above, there are attached hereto as Tables 1-5 comparative tabulations of the characteristics and properties of parent and its five offspring mutants that were developed from a single irradiated plant of "Lynwood Gold." Table 1 compares "Tinkle Bells" and its parent "Lynwood Gold". Table 2 compares "Tinkle Bells" and "Pygmy-Red". Table 3 compares "Tinkle Bells" and "Lemon-Screen". Table 4 compares "Tinkle Bells" and "Minikin". Table 5 compares "Tinkle Bells" and "Fairy Land".

TABLE 1

| | S/N 273,489 TINKLE BELLS | LYNWOOD GOLD |
|---|---|---|
| Plant: | | |
| Habit | Semi-dwarf; Upright | Tall, slender-Upright straight & erect stems |
| Size, height | 4'-4½' | 6'-7½' |
| Size, width | | |
| Vigor | Medium vigor | |
| Hardiness | Hardy Zone 6b (or lower) | |
| Productivity | Does not layer naturally (replicates from stools (no seed pods observed) | Fertile |
| Stems: | | |
| Color (young) | Yellow Green | Green |
| Color (mature) | Light brown | Brown |
| Rigidity | Sparsely lamellate between nodes - Rigid | A bit stiff; pith nodes lamellate; hollow between nodes on one year shoots |
| Leaves: | | |
| Type | Simple | |
| Color: | | |
| (young) | Medium green | Deep Green |
| (mature) | Medium green | Deep Green |
| (fall) | Faded green to yellow | |
| Shape | Elliptical | ovate lanceolate |
| tip | Acute on flower shoots accuminate on vegetative shoots | |
| base | | |
| margins | serrate on upper ⅓ near tip | |
| Size: | | |
| length | 2"-3" (with petiole) | 3-4½" |
| width | ½" | 1-1½" |
| Venation | Pinnate | |
| Flower: | | |
| Date of Flowering | Early | Late |
| Size: width | ½"-¾" at 45° angle | 1"-1½" (medium) |
| Color: | Bright Yellow (7 B) | Brillant Yellow (Lighter then its parent Spectabilis) |
| Corolla: | | |
| length | ½" open to 45° angle | |
| lobes | not reflexed during prime | Reflexed |
| Petals: number | 4; occasionally 5 or 6 | Large, broad, open Elliptic |
| Pistils: | short: anthers slightly below stigma portion of pistil | Extend well above pollen sacs (anthers) of stamens |
| Number per node: | 2; often 4 per node | |
| Insertion angle on upright stems: | buds & flowers pendulous | |
| Internodes: | ½"-1½" | Flowers almost evenly spaced on stems |
| Stress Resistance: | Disease and insect | |
| Utility Aspects: | Can force flowering suitable for container culture | |

TABLE 2

| | S/N 273,489 TINKLE BELLS | S/N: 271,666 PYGMY RED |
|---|---|---|
| Plant: | | |
| Habit | Semi-dwarf; Upright | Low, loose graceful arching to ground |
| Size, height | 4'–4½' | 3½'–4½' |
| Size, width | | 5'–6' |
| Vigor | Medium vigor | Good vigor |
| Hardiness | Hardy Zone 6b (or lower) | Hardy Zone 6b (or lower) |
| Productivity | Does not layer naturally (replicates from stools (no seed pods observed) | Readily roots where branches touch ground few seed pods |
| Stems: | | |
| Color (young) | Yellow Green | High anthocyanin |
| Color (mature) | Light brown | Purple Red (59 A) |
| Rigidity | Sparsely lamellate between nodes - Rigid | Flexible lamellate between nodes |
| Leaves: | | |
| Type | Simple | Simple |
| Color: | | |
| (young) | Medium green | Dark Green |
| (mature) | Medium green | Dark Green |
| (fall) | Faded green to yellow | Anthocyanin (maroon) expressed in full sun |
| Shape | Elliptical | Lanceolate (few lobed leaves on vegetative shoots) |
| tip | Acute on flower shoots accuminate on vegetative shoots | Accuminate |
| base | | Attenuate |
| margins | serrate on upper ⅓ near tip | Serrate |
| Size: | | |
| length | 2"–3" (with petiole) | 2"–2½" on flowering wood; to 2¾" on vegatative wood |
| width | ½" | 0.3"–0.4" on flowering wood; to 1" on vegetative wood |
| Venation | Pinnate | Pinnate |
| Flower: | | |
| Date of Flowering | Early | Intermediate |
| Size: width | ½"–¾" 45° angle | 1¼"–1½" |
| Color: | Bright Yellow (7 B) | Yellow (7A) |
| Corolla: | | |
| length | ½" open to 45° angle | |
| lobes | not reflexed during prime | Narrow |
| Petals: number | 4; occasionally 5 or 6 | 4 - sometimes 5 |
| Pistils: | short: anthers slightly below stigma portion of pistil | Extend 2/25"–3/25" above pollen sacs of stamens |
| Number per node: | 2; often 4 per node | 2 |
| Insertion angle on upright stems: | buds & flowers pendulous | |
| Internodes: | ½"–1½" | 1"–1½" (1½" even on fast growing shoots) |
| Stress Resistance: | Disease and insect | disease and insect |
| Utility Aspects: | Can force flowering suitable for container culture | |

TABLE 3

| | S/N 273,489 TINKLE BELLS | S/N 272,063 LEMON SCREEN |
|---|---|---|
| Plant: | | |
| Habit | Semi-dwarf; Upright | Tall, open and graceful; Upright, fan shape; vigorous; open foliage |
| Size, height | 4'–4½' | Up to 10' |
| Size, width | | Hardy Zone 6b (or lower) |

TABLE 3-continued

| | S/N 273,489 TINKLE BELLS | S/N 272,063 LEMON SCREEN |
|---|---|---|
| Vigor | Medium vigor | Vigorous |
| Hardiness | Hardy Zone 6b (or lower) | |
| Productivity | Does not layer naturally (replicates from stools (no seed pods observed) | Abundant Flowers/ highly sterile/pruned wood branches quickly |
| Stems: | | |
| Color (young) | Yellow Green | |
| Color (mature) | Light brown | Yellow |
| Rigidity | Sparsely lamellate between nodes - Rigid | Slightly lamellate betweeen nodes |
| Leaves: | | |
| Type | Simple | Simple |
| Color: | | |
| (young) | Medium green | Yellow green 151 B or Chartreuse (appear after flowering) |
| (mature) | Medium green | Normal green (Yellow-Green 144) whitish blotches |
| (fall) | Faded green to yellow | Greyed Purple 187 B |
| Shape | Elliptical | |
| tip | Acute on flower shoots accuminate on vegetative shoots | Accuminate |
| base | | Attenuate |
| margins | serrate on upper ⅓ near tip | Serrate |
| Size: | | |
| length | 2"–3" (with petiole) | Not distinguishing |
| width | ½" | Not distinguishing |
| Venation | Pinnate | Pinnate |
| Flower: | | |
| Date of Flowering | Early | Early |
| Size: width | ½"–¾" 45° angle | 1¼"–1¾" |
| Color: | Bright Yellow (7 B) | Yellow (6 C) |
| Corolla: | | |
| length | ½" open to 45° angle | |
| lobes | not reflexed during prime | Somewhat reflexed |
| Petals: number | 4; occasionally 5 or 6 | 4, sometimes fasciated |
| Pistils: | short: anthers slightly below stigma portion of pistil | aborted stamens &/or pistils |
| Number per node: | 2; often 4 per node | 4 to 8 |
| Insertion angle on upright stems: | buds & flowers pendulous | |
| Internodes: | ½"–1½" | 1" 2" long on flowering wood |
| Stress Resistance: | Disease and insect | Summer foliage disease & insect resistant |
| Utility Aspects: | Can force flowering suitable for container culture | Summer pruning leads to shoot with chartreuse leaves (young) |

TABLE 4

| | S/N 273,489 TINKLE BELLS | S/N 271,919 MINIKIN |
|---|---|---|
| Plant: | | |
| Habit | Semi-dwarf; Upright | Small stature, fine textured; small leaves and small stems; densely foliated |
| Size, height | 4'–4½' | 2'–2½' |
| Size, width | | 3'–4' |
| Vigor | Medium vigor | Good vigor but slow growth |
| Hardiness | Hardy Zone 6b (or lower) | Zone 6b (or lower) |
| Productivity | Does not layer naturally (replicates | Layers naturally Abundant seed pods |

TABLE 4-continued

| | S/N 273,489 TINKLE BELLS | S/N 271,919 MINIKIN |
|---|---|---|
| | from stools (no seed pods observed) | |
| Stems: | | |
| Color (young) | Yellow Green | Light green |
| Color (mature) | Light brown | Brownish green |
| Rigidity | Sparsely lamellate between nodes - Rigid | Ascending strongly lamellate between nodes |
| Leaves: | | |
| Type | Simple | Simple |
| Color: | | |
| (young) | Medium green | Bright green to dark green |
| (mature) | Medium green | Bright green to dark green |
| (fall) | Faded green to yellow | Fading green until leaf drop |
| Shape | Elliptical | Linear |
| tip | Acute on flower shoots accuminate on vegetative shoots | Accuminate |
| base | | Attenuate |
| margins | serrate on upper ⅓ near tip | Lightly serrate |
| Size: | | |
| length | 2"–3" (with petiole) | On vegetative shoots- 1½" attached to ½" long slender petiole; smaller on flowering shoots |
| width | ½" | On vegetative shoots - ¼"; |
| Venation | Pinnate | Pinnate |
| Flower: | | |
| Date of Flowering | Early | Intermediate |
| Size: width | ½"–¾" 45° angle | ½"–¾" (cup shaped) fully reflexed |
| Color: | Bright Yellow (7 B) | Yellow (9 A) |
| Corolla: | | |
| length | ½" open to 45° angle | |
| lobes | not reflexed during prime | strongly reflexed, very small |
| Petals: number | 4; occasionally 5 or 6 | 4:- short and recurved |
| Pistils: | short: anthers slightly below stigma portion of pistil | Short; 1/25" below pollen sacs of stamens |
| Number per node: | 2; often 4 per node | 2–4 |
| Insertion angle on upright stems: | buds & flowers pendulous | |
| Internodes: | ½"–1½" | Short (Flowering shoots ¼–¾" Vegetative shoots up to 2") |
| Stress Resistance: | Disease and insect | Doesn't require same degree of winter protection as most container grown plants of genre |
| Utility Aspects: | Can force flowering suitable for container culture | Blooming can be forced. Expecially suited for container culture. |

TABLE 5

| | S/N 273,489 TINKLE BELLS | S/N 271,665 FAIRY LAND |
|---|---|---|
| Plant: | | |
| Habit | Semi-dwarf; Upright | Small overall & fine textured: Closely spaced flowers & leaves Dense (young) foliage |
| Size, height | 4'–4½' | 3'–4' |
| Size, width | | 5'–6' |
| Vigor | Medium vigor | Good vigor for size |
| Hardiness | Hardy Zone 6b (or lower) | Zone 6b (or lower) |
| Productivity | Does not layer naturally (replicates from stools (no seed pods observed) | Few seed pods |
| Stems: | | |
| Color (young) | Yellow Green | Light green |
| Color (mature) | Light brown | Brownish green |
| Rigidity | Sparsely lamellate between nodes - Rigid | Very flexible lamellate between nodes |
| Leaves: | | |
| Type | Simple | Simple |
| Color: | | |
| (young) | Medium green | Medium green (fairly light) |
| (mature) | Medium green | Medium green (fairly light) |
| (fall) | Faded green to yellow | Mostly faded yellow |
| Shape | Elliptical | Lanceolate |
| tip | Acute on flower shoots accuminate on vegetative shoots | Accuminate |
| base | | Attenuate |
| margins | serrate on upper ⅓ near tip | On flowering wood; entire On vegetative wood; serrate top ⅓ |
| Size: | | |
| length | 2"–3" (with petiole) | On flowering wood: 1½"–2½" On vegatative shoots: about 3" |
| width | ½" | On flowering wood: 0.2"–0.4" On vegatative shoots 0.5–0.6" |
| Venation | Pinnate | Pinnate |
| Flower: | | |
| Date of Flowering | Early | Intermediate |
| Size: width | ½"–¾" 45° angle | ¾"–1¼" |
| Color: | Bright Yellow (7 B) | Yellow (6 A) |
| Corolla: | | |
| length | ½" open to 45° angle | |
| lobes | not reflexed during prime | Reflexed, small |
| Petals: number | 4; occasionally 5 or 6 | Generally 4-many have 5, 6, 7 and 8 on single corolla |
| Pistils: | short: anthers slightly below stigma portion of pistil | Extend 3/25" to 4/25 " above pollen sacs (anthers) of the stamen |
| Number per node: | 2; often 4 per node | 2–4 |
| Insertion angle on upright stems: | buds & flowers pendulous | |
| Internodes: | ½"–1½" | ¼" to about 1" |
| Stress Resistance: | Disease and insect | |
| Utility Aspects: | Can force flowering suitable for container culture | Very well suited for container culture |

What is claimed is:

1. A new and distinct cultivar of *Forsythia intermedia* named 'Tinkle Bells', substantially as shown and described herein.

* * * * *